United States Patent [19]
Bousquet

[11] Patent Number: 5,662,616
[45] Date of Patent: Sep. 2, 1997

[54] TRANSCUTANEOUS ACCESS DEVICE

[76] Inventor: Gerald G. Bousquet, 29 Village Sq., P.O. Box 201, Chelmsford, Mass. 01824

[21] Appl. No.: 499,543

[22] Filed: Jul. 7, 1995

[51] Int. Cl.⁶ ................................. A61M 5/32
[52] U.S. Cl. ................... 604/175; 128/DIG. 26
[58] Field of Search ......................... 604/175, 174, 604/283; 128/DIG. 26

[56] References Cited

U.S. PATENT DOCUMENTS

| | | | |
|---|---|---|---|
| 3,154,079 | 10/1964 | McKay | 604/175 |
| 4,402,694 | 9/1983 | Ash et al. | 604/891 |
| 4,416,273 | 11/1983 | Grimes | 604/283 |
| 4,593,690 | 6/1986 | Sheriden et al. | 604/283 |
| 4,621,634 | 11/1986 | Nowacki et al. | 604/283 |
| 4,863,426 | 9/1989 | Ferragamo et al. | 604/175 |
| 4,886,502 | 12/1989 | Poirier et al. . | |
| 4,897,081 | 1/1990 | Poirier et al. | 604/175 |
| 5,059,170 | 10/1991 | Cameron | 604/283 |
| 5,171,216 | 12/1992 | Dasse et al. . | |
| 5,242,415 | 9/1993 | Kantrowitz et al. | 604/175 |

*Primary Examiner*—Mark O. Polutte
*Attorney, Agent, or Firm*—Cesari and McKenna

[57] ABSTRACT

A transcutaneous access device includes a subcutaneous skirt, a transcutaneous neck and an extracutaneous telescoping sleeve all of which may be made of an inexpensive plastic material. Preferably, the skirt and neck are covered with a porous bed material which encourages the growth of tissue and collagen. The device functions as a conduit for an access catheter and is sized to minimize contact with the catheter and to allow vertical and horizontal motion of the catheter relative to the implanted portions of the access device so that torsion and stretching of the tissue adjacent to the implanted access device caused by normal body motions do not upset the biological seal that forms around the access device.

7 Claims, 1 Drawing Sheet

TRANSCUTANEOUS ACCESS DEVICE

FIELD OF THE INVENTION

This invention relates to a transcutaneous access device. It relates more particularly to a device of this type to facilitate access to the body through the skin by catheters and similar percutaneous devices.

BACKGROUND OF THE INVENTION

There has of late been increasing use of catheters to provide prolonged or repeated access to the internal organs of chronically ill patients. For example, catheters are used to access a patient's venous system for the administration of introvenous (IV) fluids, antibiotics, and chemotherapy. Catheters are also implanted in patients who require repeated access to the peritoneum for peritoneal dialysis.

Other than occlusion, the most common complications arising with long-standing implants are exit-site infection, tunnel infection, local abscesses and even sepsis. Many of these complications arise because the skin adjacent to the catheter does not heal to form a tight barrier to infection. Rather, epidermal cells tend to invaginate or migrate inward along the catheter and never form a tight biological seal around the catheter. Also, tunnels are created through which body fluids may exude thereby creating a site for infection.

In an attempt to overcome these problems, a catheter has been devised which includes a button-like skirt with a raised neck and a central hole for accommodating a tube. The tube has a corrugated segment extending above the button neck which allows the external portion of the tube to be flexed so as to absorb shocks. The skirt, including a portion of the neck thereof, is covered with a porous material, such as polyester, velour, to allow for cell infiltration. When that device is implanted, the epidermal cells tend to migrate or invaginate downward along the neck to the skirt where they form a biological seal with the collagen and subcutaneous tissue growth on the porous covering of the button; see U.S. Pat. No. 4,886,502.

While that concept was relatively successful in animals, it has had limited success in human trials because normal body motions caused stretching of the tissue adjacent to the catheter and exerted torsion on the catheter. Such movements of the tissue relative to the button, which is held stationary by the external segment of the catheter tube, results in disruption of the biological seal between the catheter and the adjacent tissue. Such disruption may also occur when the external segment of the catheter tube is moved accidentally or intentionally when connecting and disconnecting the catheter tube to the infusate source.

SUMMARY OF THE INVENTION

Accordingly, the present invention aims to provide a transcutaneous access device for a catheter which should circumvent most of the problems caused by relative movement of the catheter and the tissue surrounding the catheter.

Another object of the invention is to provide a transcutaneous access device which, when implanted, provides a tight biological seal between the device and adjacent tissue.

A further object of the invention is to provide a device of this type which reduces the risk of infection;

Yet another object of the invention is to provide a transcutaneous access device which is relatively easy to manufacture in quantity.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

The transcutaneous access device of this invention comprises a flat button with an opening therethrough and an integral upstanding tubular neck in registration with that opening. Formed as an integral extension of that neck is a pleated tube or bellows whose free end is terminated by a collar which is arranged to connect mechanically to a conventional access catheter that extends all the way through the lumen formed by the tube, neck and button of the access device.

In accordance with the invention, the lumen of the present device is large enough to provide appreciable clearance between the walls of the lumen and the catheter so as to minimize contact between the access device and the catheter.

BRIEF DESCRIPTION OF THE DRAWING

For a fuller understanding of the nature and objects of the invention, reference should be had to the following detailed description taken in connection with the accompanying drawing, in which.

DESCRIPTION OF THE PREFERRED EMBODIMENT

Figure 1:
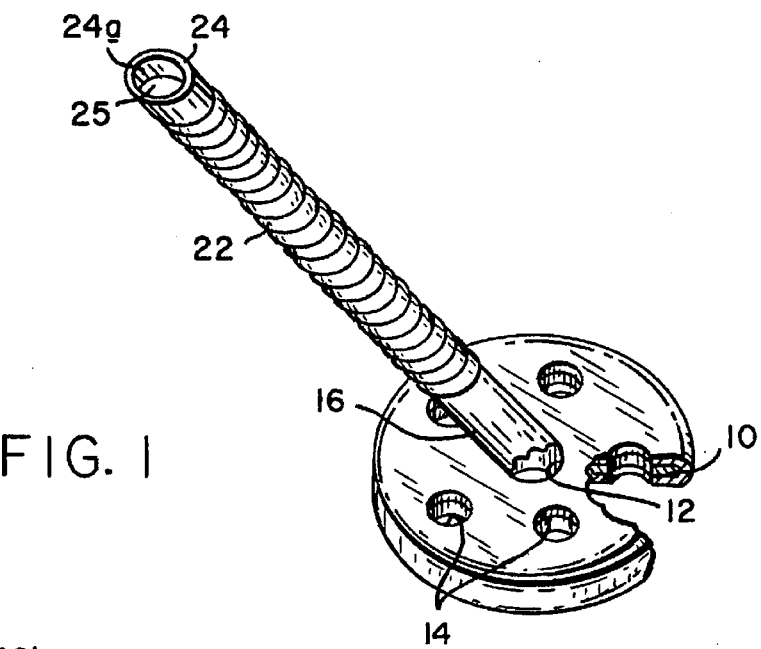
FIG. 1 is an isometric view with parts broken away of a transcutaneous access device incorporating the invention.
Figure 2:
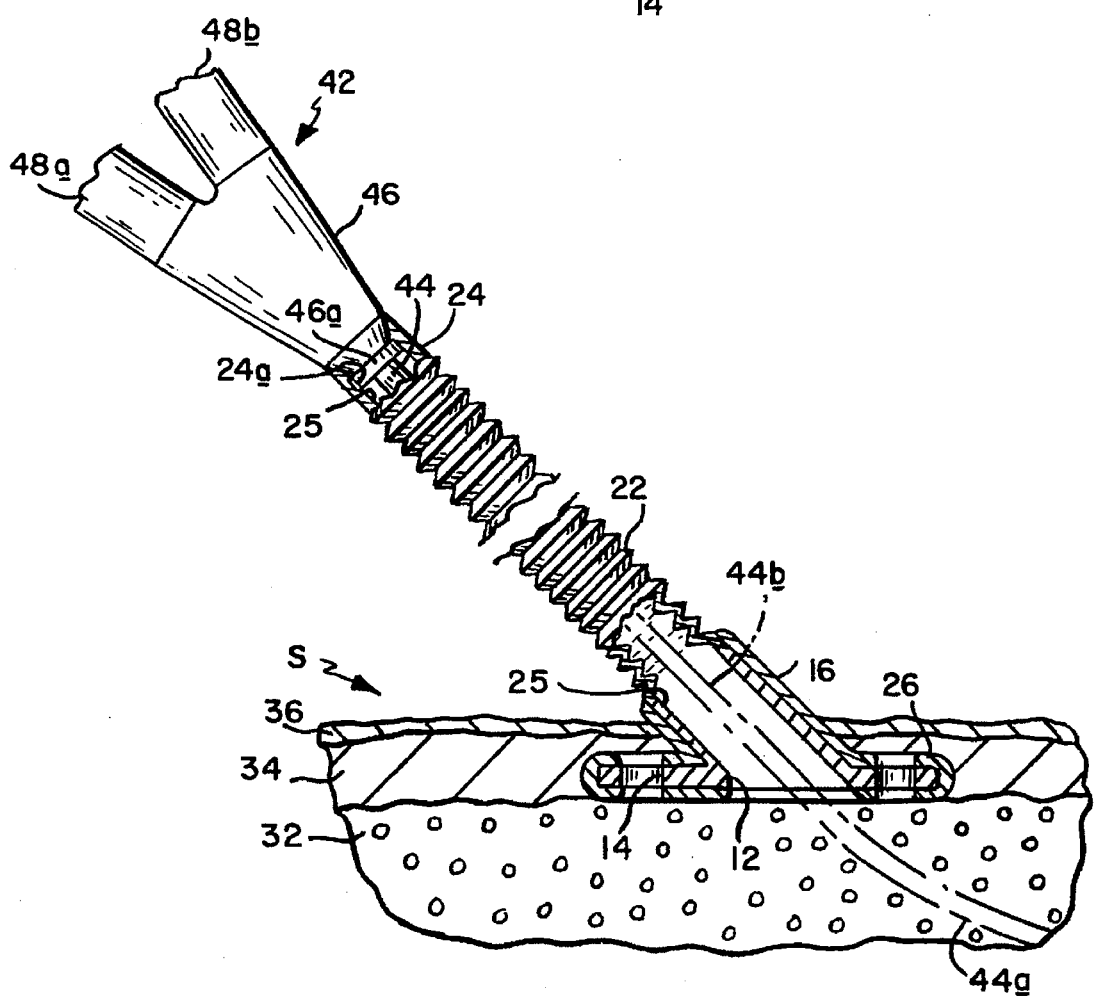
FIG. 2 is a sectional view with parts in elevation showing the FIG. 1 access device implanted in the body and ready for use.

Referring to FIGS. 1 and 2 of the drawing, my access device comprises a flat, button-like main body or skirt 10 having a central opening 12 and an army of three to five through-holes 14 distributed around opening 12. Extending out from one side of skirt 10 in registration with opening 12 is an integral, tubular neck 16 whose lumen is in registration with opening 12. In the illustrated device, the neck 16 extends out from skirt 10 at an angle; however, the neck could just as well be perpendicular to the skirt 10.

The device also includes a flexible, tubular sleeve 22 extending from the free end of neck 16. In the illustrated device, sleeve 22 is a pleated accordion-like tube which forms a bellows and which is terminated at its free end by a cylindrical collar 24. Thus, the sleeve 22 allows the collar 24 to be moved toward and away from neck 16 as well as in all directions about the longitudinal axis of neck 16. The skirt 10, neck 16, sleeve 22 and collar 24 define a continuous uniformly sized lumen 25 which extends through the entire device.

As best seen in FIG. 2, the collar 24 is formed with an internal lip 24a to provide a mechanical connection to an associated access catheter as will be described later.

The access device, including the skirt 10, neck 16, sleeve 22 and collar 24 are preferably formed of a flexible, thermally stable, biocompatible material such as flexible, medical grade polyurethane. The accordion-like sleeve 22 may be configured by placing a tubular extension of the neck 16 in a heated female mold and applying gas pressure inside the tube to force the tube walls to conform to the mold. The neck may then be secured to the button-like 10 by welding. Alternatively, the device may be molded as a unitary part.

Preferably, the entire surface of the body or skirt 10 is covered by a porous covering or bed 26 of a material such as polyester velour. Such a covered skirt 10 is available as Part No. 600K61121, from the U.S Catheter and Instrument Company of Glenfalls, N.Y. The covering encourages cell infiltration and the formation of subcutaneous tissue and collagen.

Typically, when the access device is used for peritoneal dialysis, the skirt 10 is in the order of 2.5 cm in diameter, the neck 16 is about 0.5 cm long, the sleeve 22 is about 2 to 24 cm long and the diameter of the device's lumen 25 is in the order of 0.4 to 0.8 cm. On the other hand, when the device is used for vascular access, skirt 10 may be smaller, e.g., 1 cm in diameter, with the lengths of the neck and skirt being 0.5 cm and 0.4 cm, respectively. In that event, the lumen 25 diameter may be in the order of 0.3 to 0.5 cm.

Referring to FIG. 2, the access device is implanted so that the skirt 10 is anchored in the subcutaneous tissue 32 and the neck 16 penetrates the dermal layer 34 and epidermal layer 36 of the skin S. In time, tissue growth penetrates the through-holes 14 to help anchor the access device. Those same holes also allow for fluid drainage. As noted previously, the covering 26 provides a porous bed to encourage the growth of tissue and collagen around the body 10 to provide a biological seal with the epidermal cells which migrate or invaginate along neck 16 until they reach the covering 26.

The access device is designed to be used in conjunction with an access catheter or catheter tube such as the one shown generally at 42 in FIG. 2. The illustrated catheter is a vascular access catheter. However, the catheter could just as well be a peritoneal access catheter. Suffice it to say that the catheter 42 includes a tube 44 which has an internal segment 44a which extends from the skin line along neck 16 and through body 10 to a selected infusion site such as the subclavian vein. The catheter tube also includes an external segment 44b which extends from the skin line through sleeve 22 and collar 24 to a Y-fitting 46 to which is connected a pair of fluid inlet tubes 48a and 48b so as to allow fluid from two different sources to be flowed to the catheter tube 44.

When the catheter 42 is properly seated in the access device, the lip 24a of the device's collar 24 is arranged to releasably engage over a radial flange 46a usually present at the lower end of the catheter fitting 46 to mechanically connect the catheter to the access device at the free end of the device's flexible sleeve 22. However, as noted previously, the device's lumen 25 is sized to minimize contact with the catheter tube 44 and so as not to inhibit motion of the catheter tube. Therefore, any motion of the internal catheter tube segment 44a caused by movements of the patient's body is substantially decoupled from the implanted portions of the access device, i.e., skirt 10 and neck 16. By the same token, if the external segment 44b of the catheter tube 44 should be moved accidentally or intentionally when connecting or disconnecting the catheter, the accordion sleeve 22 is able to flex, extend and contract as needed to accommodate such movement so that essentially no motion is coupled to the implanted portions of the access device. Resultantly, a tight biological seal is maintained between the access device and the surrounding tissue.

Indeed, actual experiments with prototype devices have shown that there are no signs of infection at the implantation sites even after the devices have been in place for prolonged periods.

As seen from the foregoing, my transcutaneous access device is, for the most part, a molded plastic part which can be made in quantity relatively easily and inexpensively. Therefore, it should find wide application wherever it is necessary to maintain catheters in situ for a long period of time.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention described herein.

What is claimed is:

1. A transcutaneous access device and catheter comprising
   a cylindrical tubular neck having opposite ends and a lumen, said neck adapted to protrude from the skin;
   an annular skirt at one end of the neck for anchoring in subcutaneous tissue;
   a flexible, extensible sleeve extending from the opposite end of the neck, said sleeve having a free end and defining with said neck a lumen through the device;
   a catheter tube received in said lumen as defined by said sleeve and said neck and having opposite ends, and
   connector means for releasably connecting the free end of the sleeve to the catheter tube.

2. The device defined in claim 1 and further including a bed of porous material covering said neck and said skirt.

3. The device defined in claim 2 wherein the porous material is polyester velour.

4. The device defined in claim 1 and further including an array of through-holes in said skirt.

5. The device and catheter defined in claim 1 wherein the connector means comprises
   a first surface at the free end of said sleeve, and
   a second surface on the catheter tube, said first and second surfaces inter-fitting with each other so as to releasably connect the free end of the sleeve to the catheter tube.

6. The device defined in claim 1 wherein said skirt, neck and sleeve are of flexible medical grade polyurethane.

7. The device and catheter defined in claim 5 wherein said first surface is constituted by
   a tubular collar at the free end of the sleeve, and
   a circular lip formed on the inner surface of the collar for interfitting with the second surface.

* * * * *